United States Patent
Eimerl et al.

(10) Patent No.: US 8,291,913 B2
(45) Date of Patent: *Oct. 23, 2012

(54) ADAPTIVE CONTROL OF OPTICAL PULSES FOR LASER MEDICINE

(75) Inventors: David Eimerl, Livermore, CA (US); Leonard C. DeBenedictis, Palo Alto, CA (US)

(73) Assignee: Reliant Technologies, Inc., Hayward, CA (US)

( * ) Notice: Subject to any disclaimer, the term of this patent is extended or adjusted under 35 U.S.C. 154(b) by 1101 days.

This patent is subject to a terminal disclaimer.

(21) Appl. No.: 12/228,968

(22) Filed: Aug. 18, 2008

(65) Prior Publication Data

US 2009/0137994 A1 May 28, 2009

Related U.S. Application Data

(63) Continuation of application No. 10/868,134, filed on Jun. 14, 2004, now Pat. No. 7,413,572.

(51) Int. Cl.
*A61B 19/00* (2006.01)
*A61B 18/18* (2006.01)
(52) U.S. Cl. ............... 128/898; 606/9; 607/88
(58) Field of Classification Search ............... 606/3–12; 607/88, 89, 92, 94; 128/898
See application file for complete search history.

(56) References Cited

U.S. PATENT DOCUMENTS

| | | | |
|---|---|---|---|
| 3,622,743 A | 11/1971 | Muncheryan | |
| 3,721,486 A | 3/1973 | Bramley | |
| 4,122,853 A | 10/1978 | Smith | |
| 4,396,285 A | 8/1983 | Presta et al. | |
| 4,556,057 A | 12/1985 | Hiruma et al. | |
| 4,573,465 A | 3/1986 | Sugiyama et al. | |
| 4,587,396 A | 5/1986 | Rubin | |
| 4,641,650 A | 2/1987 | Mok | |
| 4,653,495 A | 3/1987 | Nanaumi | |
| 4,672,969 A | 6/1987 | Dew | |
| 4,718,416 A | 1/1988 | Nanaumi | |
| 4,733,660 A | 3/1988 | Itzkan | |
| 4,775,361 A | 10/1988 | Jacques et al. | |
| 4,917,083 A | 4/1990 | Harrington et al. | |
| 4,930,504 A | 6/1990 | Diamantopoulos et al. | |
| 4,976,709 A | 12/1990 | Sand | |
| 5,000,752 A | 3/1991 | Hoskin et al. | |
| 5,002,051 A | 3/1991 | Dew et al. | |
| 5,076,669 A | 12/1991 | Black et al. | |

(Continued)

FOREIGN PATENT DOCUMENTS

EP 0880941 B1 12/2001

(Continued)

OTHER PUBLICATIONS

US 6,344,051, Withdrawn.
U.S. Appl. No. 60/458,770, Manstein et al.
Andersen, Dan E. et al., "System for the automated photothermal treatment of cutaneous vascular lesions," *Journal of Biomedical Optics* 9(2) (Mar./Apr. 2004), pp. 308-314.
Anderson, R. R. et al., "Laser-Tissue Interactions," Chapter 1 of *Cosmetic Laser Surgery*, Mosby, Inc., 2000, pp. 1-30.

(Continued)

*Primary Examiner* — Ahmed Farah
(74) *Attorney, Agent, or Firm* — Wood, Herron & Evans, LLP

(57) ABSTRACT

Tissue is treated by irradiating it with a sequence of optical pulses that are directed in sequence to various sites on the tissue. During the irradiation sequence, one or more tissue properties are measured at a site(s) that has already been irradiated. These measurements are used to adjust the parameters of subsequent optical pulses in the sequence.

34 Claims, 10 Drawing Sheets

U.S. PATENT DOCUMENTS

| | | |
|---|---|---|
| 5,104,392 A | 4/1992 | Kittrell |
| 5,106,387 A | 4/1992 | Kittrell et al. |
| 5,114,218 A | 5/1992 | Black et al. |
| 5,128,509 A | 7/1992 | Black et al. |
| 5,139,494 A | 8/1992 | Freiberg |
| 5,144,630 A | 9/1992 | Lin |
| 5,151,600 A | 9/1992 | Black |
| 5,163,935 A | 11/1992 | Black et al. |
| 5,163,936 A | 11/1992 | Black et al. |
| 5,178,617 A | 1/1993 | Kuizenga et al. |
| 5,184,156 A | 2/1993 | Black et al. |
| 5,192,278 A | 3/1993 | Hayes et al. |
| 5,282,797 A | 2/1994 | Chess |
| 5,302,259 A | 4/1994 | Birngruber |
| 5,312,395 A | 5/1994 | Tan et al. |
| 5,312,396 A | 5/1994 | Feld et al. |
| 5,318,024 A | 6/1994 | Kittrell et al. |
| 5,330,517 A | 7/1994 | Mordon et al. |
| 5,336,217 A | 8/1994 | Buys et al. |
| 5,339,347 A | 8/1994 | Slatkin et al. |
| 5,360,447 A | 11/1994 | Koop |
| 5,382,770 A | 1/1995 | Black et al. |
| 5,382,986 A | 1/1995 | Black |
| 5,411,502 A | 5/1995 | Zair |
| 5,419,323 A | 5/1995 | Kittrell et al. |
| 5,421,337 A | 6/1995 | Richards-Kortum et al. |
| 5,423,803 A | 6/1995 | Tankovich et al. |
| 5,449,882 A | 9/1995 | Black et al. |
| 5,474,549 A | 12/1995 | Ortiz et al. |
| 5,505,726 A | 4/1996 | Meserol |
| 5,531,740 A | 7/1996 | Black |
| 5,546,214 A | 8/1996 | Black et al. |
| 5,558,666 A | 9/1996 | Dewey et al. |
| 5,562,100 A | 10/1996 | Kittrell et al. |
| 5,582,752 A | 12/1996 | Zair |
| 5,586,981 A | 12/1996 | Hu |
| 5,595,568 A | 1/1997 | Anderson et al. |
| 5,611,795 A | 3/1997 | Slatkine et al. |
| 5,616,140 A | 4/1997 | Prescott |
| 5,618,284 A | 4/1997 | Sand |
| 5,618,285 A | 4/1997 | Zair |
| 5,624,434 A | 4/1997 | Abergel et al. |
| 5,628,744 A | 5/1997 | Coleman et al. |
| 5,632,741 A | 5/1997 | Zavislan et al. |
| 5,643,252 A | 7/1997 | Waner et al. |
| 5,653,706 A | 8/1997 | Zavislan et al. |
| 5,655,547 A | 8/1997 | Karni |
| 5,707,403 A | 1/1998 | Grove et al. |
| 5,713,364 A | 2/1998 | DeBaryshe et al. |
| 5,733,278 A | 3/1998 | Slatkine et al. |
| 5,735,844 A | 4/1998 | Anderson et al. |
| 5,746,735 A | 5/1998 | Furumoto et al. |
| 5,759,200 A | 6/1998 | Azar |
| 5,779,696 A | 7/1998 | Berry et al. |
| 5,786,924 A | 7/1998 | Black et al. |
| 5,798,498 A | 8/1998 | Zair |
| 5,807,386 A | 9/1998 | Slatkine et al. |
| 5,810,801 A | 9/1998 | Anderson et al. |
| 5,814,042 A | 9/1998 | Zair |
| 5,817,089 A | 10/1998 | Tankovich et al. |
| 5,830,208 A | 11/1998 | Muller |
| 5,843,073 A | 12/1998 | Sinofsky |
| 5,860,967 A | 1/1999 | Zavislan et al. |
| 5,860,968 A | 1/1999 | Wojcik et al. |
| 5,865,754 A | 2/1999 | Sevick-Muraca et al. |
| 5,879,326 A | 3/1999 | Godshall et al. |
| 5,885,211 A | 3/1999 | Eppstein et al. |
| 5,897,549 A | 4/1999 | Tankovich |
| 5,908,415 A | 6/1999 | Sinofsky |
| 5,925,035 A | 7/1999 | Tankovich |
| 5,938,657 A | 8/1999 | Assa et al. |
| 5,947,956 A | 9/1999 | Karell |
| 5,951,543 A | 9/1999 | Brauer |
| 5,957,915 A | 9/1999 | Trost |
| 5,964,749 A | 10/1999 | Eckhouse et al. |
| 5,968,033 A | 10/1999 | Fuller et al. |
| 5,970,983 A | 10/1999 | Karni et al. |
| 5,983,900 A | 11/1999 | Clement et al. |
| 5,984,915 A | 11/1999 | Loeb et al. |
| 5,995,265 A | 11/1999 | Black et al. |
| 5,995,866 A | 11/1999 | Lemelson |
| 6,011,809 A | 1/2000 | Tosaka |
| 6,015,404 A | 1/2000 | Altshuler et al. |
| 6,022,316 A | 2/2000 | Eppstein et al. |
| 6,027,496 A | 2/2000 | Loomis et al. |
| RE36,634 E | 3/2000 | Ghaffari |
| 6,036,684 A | 3/2000 | Tankovich et al. |
| 6,050,990 A | 4/2000 | Tankovich et al. |
| 6,059,820 A | 5/2000 | Baronov |
| 6,063,108 A | 5/2000 | Salansky et al. |
| 6,074,384 A | 6/2000 | Brinkmann |
| 6,083,217 A | 7/2000 | Tankovich |
| 6,096,029 A | 8/2000 | O'Donnell, Jr. |
| 6,096,031 A | 8/2000 | Mitchell et al. |
| 6,104,959 A | 8/2000 | Spertell |
| 6,106,514 A | 8/2000 | O'Donnell, Jr. |
| RE36,872 E | 9/2000 | Zair |
| 6,113,559 A | 9/2000 | Klopotek |
| 6,120,497 A | 9/2000 | Anderson et al. |
| 6,142,939 A | 11/2000 | Eppstein |
| 6,149,644 A | 11/2000 | Xie |
| 6,149,645 A | 11/2000 | Tobinick |
| 6,152,917 A | 11/2000 | Tankovich |
| 6,162,211 A | 12/2000 | Tankovich et al. |
| 6,162,213 A | 12/2000 | Stewart |
| 6,165,170 A | 12/2000 | Wynne et al. |
| 6,168,590 B1 | 1/2001 | Neev |
| 6,171,302 B1 | 1/2001 | Talpalriu et al. |
| 6,173,202 B1 | 1/2001 | Eppstein |
| 6,176,842 B1 | 1/2001 | Tachibana et al. |
| 6,176,854 B1 | 1/2001 | Cone |
| 6,183,773 B1 | 2/2001 | Anderson |
| 6,197,020 B1 | 3/2001 | O'Donnell, Jr. |
| 6,208,673 B1 | 3/2001 | Miyake |
| 6,208,886 B1 | 3/2001 | Alfano et al. |
| 6,219,575 B1 | 4/2001 | Nemati |
| 6,235,015 B1 | 5/2001 | Mead, III et al. |
| 6,241,753 B1 | 6/2001 | Knowlton |
| 6,245,060 B1 | 6/2001 | Loomis et al. |
| 6,248,103 B1 | 6/2001 | Tannenbaum et al. |
| 6,251,099 B1 | 6/2001 | Kollias et al. |
| 6,251,100 B1 | 6/2001 | Flock et al. |
| 6,267,771 B1 | 7/2001 | Tankovich et al. |
| 6,273,884 B1 | 8/2001 | Altshuler et al. |
| 6,273,885 B1 | 8/2001 | Koop et al. |
| 6,293,911 B1 | 9/2001 | Imaizumi et al. |
| 6,315,772 B1 | 11/2001 | Marchitto et al. |
| 6,325,769 B1 | 12/2001 | Klopotek |
| 6,328,733 B1 | 12/2001 | Trost |
| 6,350,261 B1 | 2/2002 | Domankevitz et al. |
| 6,375,672 B1 | 4/2002 | Aksan et al. |
| 6,387,089 B1 | 5/2002 | Kreindel et al. |
| 6,391,022 B1 | 5/2002 | Furumoto et al. |
| 6,395,000 B1 | 5/2002 | Mitchell et al. |
| 6,406,474 B1 | 6/2002 | Neuberger et al. |
| 6,413,267 B1 | 7/2002 | Dumoulin-White et al. |
| 6,436,127 B1 | 8/2002 | Anderson et al. |
| 6,443,946 B2 | 9/2002 | Clement et al. |
| 6,443,978 B1 | 9/2002 | Zharov |
| 6,445,491 B2 | 9/2002 | Sucha et al. |
| 6,468,229 B1 | 10/2002 | Grace et al. |
| 6,475,138 B1 | 11/2002 | Schecther et al. |
| 6,508,813 B1 | 1/2003 | Altshuler |
| 6,511,475 B1 | 1/2003 | Altshuler et al. |
| 6,514,244 B2 | 2/2003 | Pope et al. |
| 6,514,278 B1 | 2/2003 | Hibst et al. |
| 6,517,532 B1 | 2/2003 | Altshuler et al. |
| 6,529,543 B1 | 3/2003 | Anderson et al. |
| 6,530,915 B1 | 3/2003 | Eppstein et al. |
| 6,533,776 B2 | 3/2003 | Asah et al. |
| 6,537,270 B1 | 3/2003 | Elbrecht et al. |
| 6,562,004 B1 | 5/2003 | Doukas et al. |
| 6,569,155 B1 | 5/2003 | Connors et al. |
| 6,569,156 B1 | 5/2003 | Tankovich et al. |
| 6,572,637 B1 | 6/2003 | Yamazaki et al. |
| 6,575,963 B1 | 6/2003 | Van Saarloos et al. |
| 6,579,283 B1 | 6/2003 | Tobinick |

| | | | |
|---|---|---|---|
| 6,585,725 B1 | 7/2003 | Mukai | |
| 6,605,080 B1 | 8/2003 | Altshuler et al. | |
| 6,607,523 B1 | 8/2003 | Asah et al. | |
| 6,613,040 B2 | 9/2003 | Tankovich et al. | |
| 6,613,042 B1 | 9/2003 | Tankovich et al. | |
| 6,632,219 B1 | 10/2003 | Baranov et al. | |
| 6,652,512 B2 | 11/2003 | Ota | |
| 6,653,618 B2 | 11/2003 | Zenzie | |
| 6,659,999 B1 | 12/2003 | Anderson et al. | |
| 6,676,654 B1 | 1/2004 | Balle-Petersen et al. | |
| 6,680,999 B1 | 1/2004 | Garcia | |
| 6,685,699 B1 | 2/2004 | Eppstein et al. | |
| 6,695,835 B2 | 2/2004 | Furuno et al. | |
| 6,706,032 B2 | 3/2004 | Weaver et al. | |
| 6,717,102 B2 | 4/2004 | Neev et al. | |
| 6,723,090 B2 | 4/2004 | Altshuler et al. | |
| 6,743,211 B1 | 6/2004 | Prausnitz et al. | |
| 6,746,444 B2 | 6/2004 | Key | |
| 6,758,845 B1 | 7/2004 | Weckwerth et al. | |
| 6,824,540 B1 | 11/2004 | Lin | |
| 6,836,278 B2 | 12/2004 | Saito et al. | |
| 6,881,212 B1 | 4/2005 | Clement et al. | |
| 6,991,644 B2 | 1/2006 | Spooner et al. | |
| 7,006,874 B2 | 2/2006 | Knowlton et al. | |
| 7,025,765 B2 * | 4/2006 | Balbierz et al. | 606/41 |
| 7,204,832 B2 | 4/2007 | Altshuler et al. | |
| 7,217,266 B2 * | 5/2007 | Anderson et al. | 606/12 |
| 7,413,572 B2 * | 8/2008 | Eimerl et al. | 607/88 |
| 2001/0007068 A1 | 7/2001 | Ota et al. | |
| 2001/0023351 A1 | 9/2001 | Eilers et al. | |
| 2002/0002367 A1 | 1/2002 | Tankovich et al. | |
| 2002/0062142 A1 | 5/2002 | Knowlton | |
| 2002/0091377 A1 | 7/2002 | Anderson et al. | |
| 2002/0138072 A1 | 9/2002 | Black et al. | |
| 2002/0161357 A1 | 10/2002 | Anderson et al. | |
| 2002/0173780 A1 | 11/2002 | Altshuler et al. | |
| 2003/0032950 A1 | 2/2003 | Altshuler et al. | |
| 2003/0034959 A1 | 2/2003 | Davis et al. | |
| 2003/0055413 A1 | 3/2003 | Altshuler et al. | |
| 2003/0181893 A1 | 9/2003 | Neuberger | |
| 2004/0000316 A1 | 1/2004 | Knowlton et al. | |
| 2004/0015157 A1 | 1/2004 | Connors et al. | |
| 2004/0030332 A1 | 2/2004 | Knowlton et al. | |
| 2004/0045948 A1 | 3/2004 | Shalev et al. | |
| 2004/0133251 A1 | 7/2004 | Altshuler et al. | |
| 2004/0143247 A1 | 7/2004 | Anderson et al. | |
| 2004/0147984 A1 | 7/2004 | Altshuler et al. | |
| 2004/0152943 A1 | 8/2004 | Zimmerman et al. | |
| 2004/0162549 A1 | 8/2004 | Altshuler | |
| 2005/0015077 A1 | 1/2005 | Kuklin et al. | |
| 2005/0049582 A1 | 3/2005 | DeBenedictis et al. | |
| 2005/0137584 A1 | 6/2005 | Lemchen | |
| 2005/0143719 A1 | 6/2005 | Sink | |
| 2005/0154382 A1 | 7/2005 | Altshuler et al. | |
| 2006/0011024 A1 | 1/2006 | Azar et al. | |
| 2006/0089556 A1 * | 4/2006 | Bambot et al. | 600/476 |

FOREIGN PATENT DOCUMENTS

| | | |
|---|---|---|
| WO | WO 99/27997 A1 | 6/1999 |
| WO | WO 00/53261 A1 | 9/2000 |
| WO | WO 00/67917 A1 | 11/2000 |
| WO | WO 01/26573 A1 | 4/2001 |
| WO | WO 01/39834 A1 | 6/2001 |
| WO | WO 01/74265 | 10/2001 |
| WO | WO 02/22035 | 3/2002 |
| WO | WO 2004/037068 A1 | 5/2004 |
| WO | WO 2004/084752 A2 | 10/2004 |
| WO | WO 2004/086947 A2 | 10/2004 |
| WO | WO 2004/088700 A2 | 10/2004 |

OTHER PUBLICATIONS

Apfelberg, David B. et al., "Dot or Pointillistic Method for Improvement in Results of Hypertrophic Scarring in the Argon Laser Treatment of Portwine Hemangiomas", Lasers in Surgery and Medicine, vol. 6 (1987), pp. 552-558.

Apfelberg, David B., "Intralesional Laser Photocoagulation—Sterioids as an Adjunct to Surgery for Massive Hermangiomas and Vascular Malformations", Annals of Plastic Surgery, vol. 35, No. 2 (Aug. 1995), pp. 144-149.

Dimitrios, C. Nikas et al., "Fluorescent Imaging in a Glioma Model in Vivo," Lasers in Surgery and Medicine, vol. 29, 2001. pp. 11-17.

Fitzpatrick, R.E. "Laser Hair Transplantation. Tissue Effects of Laser Parameters," Dermatol. Surg., Dec. 1995, pp. 1042-1046, vol. 21, No. 12.

Fujii, H. et al., "Fiber bundle scanner for laser photocoagulation treatment," Optics and Laser Technology, Feb. 1982, pp. 39-40.

Fujii, Hitoshi et al., "Multispot laser photocoagulation system using a fiber bundle scanner," Applied Optics, vol. 21, No. 19, Oct. 1, 1982, pp. 3437-3442.

Grevelink, J.M., "Laser Hair Transplantation," Dermatologic Clinics, Jul. 1, 1997, pp. 479-486, vol. 15, Issue 3.

Guo, Ruixiang et al., "Application of an all-solid-state, frequency-doubled Nd:YAP laser to the generation of twin beams at 1080 nm," Applied Optics, vol. 41, No. 12, Apr. 20, 2002, pp. 2304-2307.

Huzaira, M. et al., "Intradermal Focusing of Near-Infrared Optical Pulses: A New Approach for Non-Ablative Laser Therapy," ASLMS 2003—ABS66, 1 page.

Israel Patent Application Office Action, Israel Patent Application No. 168231, Dec. 8, 2008, 4 pages.

Khatri, K. et al., "Treatment of Rhytids with Subsurface-Focused Er:YLF Laser," ASLMS 2003—Abs68, 1 page.

Lakowicz, Joseph R. et al., "Intensified Fluorescence: Radiative decay engineering uses metal particles to enhance fluorescence, suggesting myriad new applications in biotechnology and chemistry," Photonics Spectra, Oct. 2001, A Laurin Publication, Biotechnology, pp. 97-103.

Manstein, Dieter et al., "Fractional Photothermoysis: A New Concept for Cutaneous Remodeling Using Microscopic Patterns of Thermal Injury," Lasers in Surgery and Medicine, vol. 34 (2004), pp. 426-438.

McKenzie, A.L., "A Three-Zone Model of Tissue Damage by a CO2 Laser," Phys. Med. Boil, 1986, pp. 967-983, vol. 31, No. 9.

Mordon, Serge et al., "Using a 'Non Uniform Pulse Sequence' can Improve Selective Coagulation with a Nd;YAG Laser (1.06 micron) Thanks to Met-Hemoglobin Absorption: A Clinical Study on Blue Leg Veins," Lasers in Surgery and Medicine, vol. 32 (2003), pp. 160-170.

Naess, E. et al., "Computer-Assisted Laser Photocoagulation of the Retina—a Hybrid Tracking Approach," Journal of Biomedical Optics, Apr. 2002, pp. 179-189, vol. 7, No. 2.

Ott, Dale, "Fluorescent proteins reveal food contamination," Biophotonics International, Nov. 2001, pp. 8-9.

Ou, Z.Y. et al., "85% efficiency for cw frequency doubling from 1.08 to 0.54 microns," Optics Letters, vol. 17, No. 9, May 1, 1992, pp. 640-642.

Partovi, F. et al., "A Model for Thermal Ablation of Biological Tissue Using Laser Radiation," Lasers in Surgery and Medicine, 1987, pp. 141-154, vol. 7.

PCT International Search Report and Written Opinion, PCT/US07/03694, Feb. 22, 2008, 12 pages.

PCT International Search Report and Written Opinion, PCT/US05/47028, Jul. 8, 2008, 6 pages.

Rubach, B.W. et al., "Histological and Clinical Evaluation of Facial Resurfacing Using a Carbon Dioxide Laser with the Computer Pattern Generator," Arch. Otolaryngol. Head Neck Surg., Sep. 1997, pp. 929-934, vol. 123, No. 9.

Unger, W.P. et al., "Laser Hair Transplantation," J. Dermatol. Surg. Oncol., Aug. 1994, pp. 515-521, vol. 20, No. 8.

Unger, W.P. "Laser Hair Transplantation III. Computer-Assisted Laser Transplantating," Dermatol. Surg. Dec. 1995, pp. 1047-1055, vol. 21, No. 12.

Wyant, J.C., "Rotating Diffraction Grating Laser Beam Scanner", Applied Optics, vol. 14, May 1975, pp. 1057-1058.

Manstein, D. et al., "Spatially Confined Photothermolysis of Dermal Targets Using an IR-fiberlaser in Combination with Focusing and Contact Cooling," American Society for Laser Medicine and Surgery, 2002, Abstract 92, p. 28.

* cited by examiner

Location of the head of the hand-piece
relative to the tissue surface

*Figure 4: A possible utilization of the hand-piece surface in closest proximity to the tissue*

*Figure 5: A possible layout of end-point detect signal sources and detectors in the hand-piece head, including a possible imaging system, and a passive detection system.*

ADAPTIVE CONTROL OF OPTICAL PULSES FOR LASER MEDICINE

CROSS-REFERENCE TO RELATED APPLICATION(S)

This application is a continuation of U.S. patent application Ser. No. 10/868,134, "Adaptive Control of Optical Pulses for Laser Medicine," filed Jun. 14, 2004. The subject matter of all of the foregoing is incorporated herein by reference in its entirety.

BACKGROUND OF THE INVENTION

1. Field of the Invention

This invention relates to the field of medicine in which optical pulses are used to treat human tissue, including for example laser dermatology, laser surgery, and laser medicine. More specifically, this invention relates to controlling the optical pulses used in the treatment.

2. Description of the Related Art

The use of optical pulses to treat human tissue is now quite widespread. In these procedures, optical pulses from a suitable optical source, such as a laser, a lamp, or an electromagnetic pulse generator, are directed at human tissue. The optical pulses typically pass through the surface of the tissue and into the subsurface layers of the tissue, where beneficial changes occur in the tissue in response to the passage of the optical pulse.

A common challenge facing practitioners of this type of procedure in vivo is the variation in tissue response from one treatment to the next. Variations may be the result of differences between individuals. Differences between patients may exist for many reasons, including being associated with the general health, age, sex, race and/or the history of sun exposure. Variations may also be the result of differences in tissue type and/or responsivity within a single individual. Trends may be seen where the response of the tissue depends on the presence of bioagents in the tissue, such as melanin, hemoglobin, interstitial fluid, fatty matter, or foreign matter such as tattoo dyes. For example, in one common technique, optical pulses in the wavelength range 400-800 nm are used to heat the tissue below the surface of the human skin, which exhibits change as a result of the elevated temperature. The amount of melanin in the skin greatly affects the penetration and heating effect of the optical pulses. Often the practitioner proceeds without knowing precisely what the responsiveness of the tissue will be. As a result, there is an increased risk that the tissue will be over- or under-treated.

Accordingly, a significant concern for practitioners is the correct selection of the parameters of the optical pulses used to irradiate the tissue. These parameters can include, but are not limited to, the pulse energy, spot size, wavelength, temporal pulse shape, spatial pulse shape, pulse duration, focus location, depth of focus, optical polarization, or angle of incidence on the treatment region. These parameters can also include aggregate quantities, such as the number or density of optical pulses directed to a site or the total energy deposited at a site. Pulse parameters such as the spacing between pulses, the separation between sequentially irradiated sites, and the shape of a sequence of pulses can also be adjusted. For each treatment, the parameters ideally should be selected to produce the desired beneficial effect, taking into account all variations regardless of the cause. The concern arises from the significant variation in tissue response. Irradiation parameters that produce no effect in one case may possibly produce a damaging effect in another. Thus, the effectiveness of the treatment often depends of the ability of the practitioner to judge or otherwise determine the appropriate pulse parameters before treatment.

The process of detecting the tissue response, and thereby determining when the treatment should be terminated, is often referred to as "end-point detection." Methods to detect tissue response to a single pulse in real-time have been suggested, but many methods are unsuitable for end-point detection or other types of control, being either too inaccurate or too slow to give timely guidance to the practitioner. For example, in laser dermatology using laser pulses of 1 millisecond pulse length, the time available to diagnose the tissue response is only a few hundred microseconds. Few, if any, techniques are suitable for end-point detection of subsurface tissue response in this short time frame.

Another method sometimes used in current practice is to treat a small, relatively unnoticeable portion of the tissue to test the optical pulse parameters. Another method simply relies on the practitioner's skills of observation, experience and judgment. Yet another method makes measurements of related optical properties of the tissue immediately prior to treatment, and this data is used in combination with the practitioner's judgment, skills and experience to set the pulse parameters. These methods have a variable level of reliability because they are inexact and do not always account for variables that can significantly affect the pulse parameters. Even treatments of the same area of the same patient's tissue by the same practitioner on different occasions may require different optical pulse parameters. As another example, pre-testing small regions of tissue may require several attempts before the correct settings are determined, and, to the extent that the tested regions are located at some distance from or are otherwise different from the actual region to be treated, the results might be inaccurate.

Thus, there is a need for systems and methods for real-time control of optical pulses used to treat tissue.

SUMMARY OF THE INVENTION

The present invention overcomes the limitations of the prior art as follows. Tissue is treated by irradiating it with a sequence of optical pulses that are directed in sequence to various sites on the tissue. Multiple pulses can irradiate multiple sites simultaneously. During the irradiation sequence, one or more tissue properties are measured at a site(s) that has already been irradiated. These measurements are used to adjust the parameters of subsequent optical pulses in the sequence.

Various tissue properties, measurement techniques, pulse parameters and control algorithms relating the parameters and measured properties can be used. Some examples of tissue properties include optical properties (e.g., birefringence, reflectivity), electrical capacitance, and fraction of various materials (e.g., water, melanin). Some examples of pulse parameters include pulse energy, shape, wavelength, and number of pulses per site. Many other examples have been discussed previously or are discussed in further detail below.

In one approach, end-point detection is used. For example, a predetermined value (or range of values) of the tissue property may be defined as the end-point of the treatment and the pulse parameters are then adjusted to remain within the desired range. In one embodiment, measurements are taken before and after treatment. The "before" sample can be taken at a site that has not yet been irradiated and the "after" sample at a site after irradiation. Alternately, "before" and "after" samples can be taken at the same site, but before and after irradiation. If multiple measurements are made, different averaging techniques can be used.

Artificial intelligence approaches can be used to actively adjust pulse parameters but can also actively determine tissue characteristics, which can be stored for later use. For example, the data can be used to treat the same type of tissue at a later date. As another example, patient-specific data can be stored for subsequent treatment of the same patient.

Other aspects of the invention include devices and systems corresponding to the above.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION OF THE PREFERRED EMBODIMENTS

Figure 1:
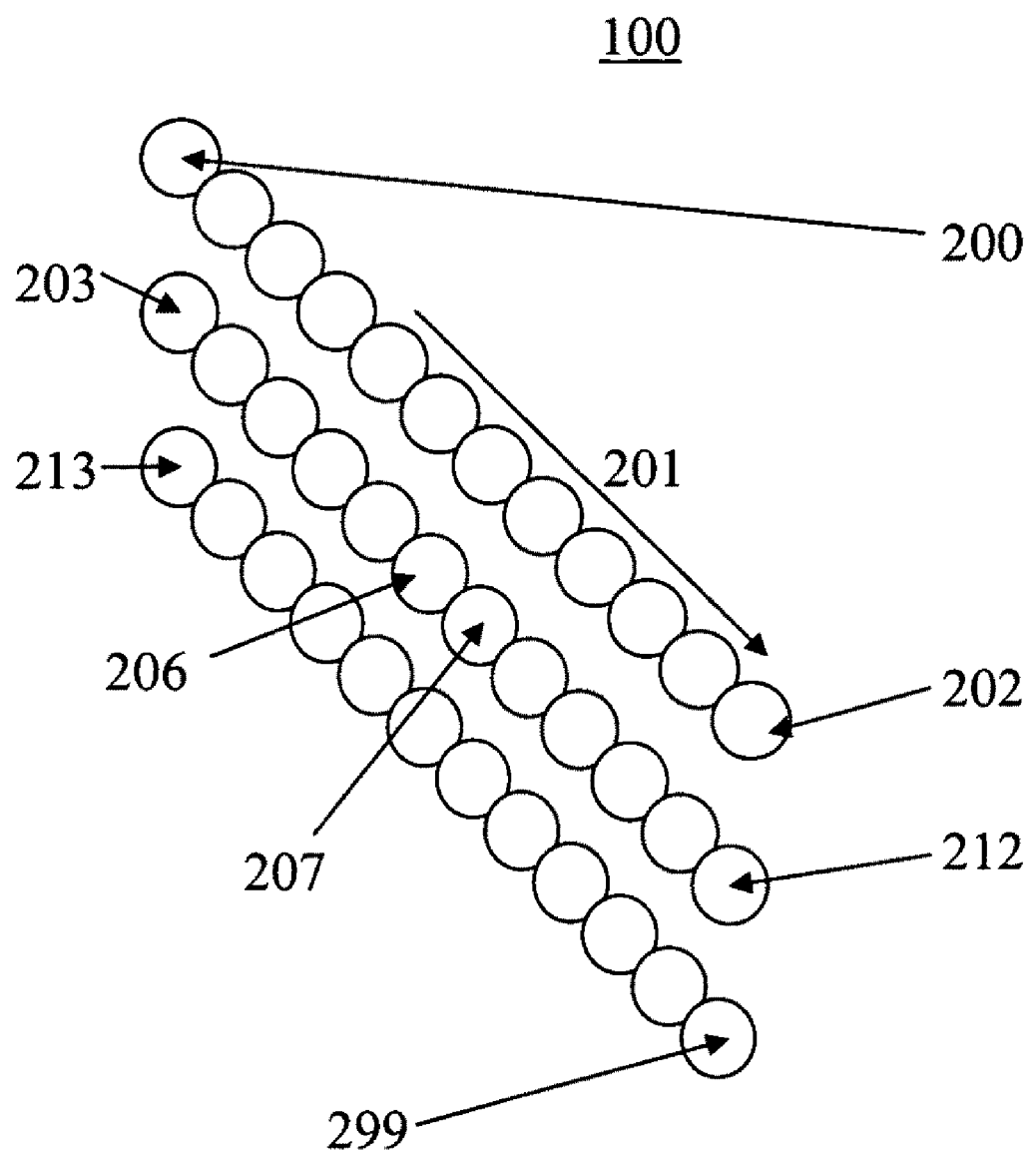
FIG. 1 is a diagram showing an irradiation pattern suitable for use with the invention.

FIG. 1 is a diagram showing an irradiation pattern 100 suitable for use with the invention. The pattern includes a large number of sites, each indicated by a circle. These sites are irradiated in one treatment or scan of the tissue. A sequence of optical pulses is directed to the sites in sequence. In FIG. 1, the irradiation sequence starts from the top left with site 200 and proceeds diagonally down to the right in the direction 201 to the last site 202 in the first row. It then returns to the top left site 203 of the next row and continues down and to the right to site 212. The sequence continues until the last site 299 is irradiated.

FIG. 1 is an example. Many other patterns of sites, irradiation sequences, and sizes, shapes and locations of the sites are also suitable for use with the invention. For example, the sites may overlap, or be widely separated, or they may just touch their neighbor, as illustrated in FIG. 1. Sites may overlap at the tissue surface or not; they may overlap below the surface or not. Sites can also have different depth profiles and different three-dimensional shapes. Sites are not required to have the same shape. While the layout of sites in FIG. 1 creates a regular pattern, irregular and quasi-regular patterns can also be used. While the irradiation sequence in FIG. 1 is simple and predetermined, non-deterministic, chaotic, and more complex irradiation sequences can also be used. Moreover, while each site is irradiated only once in the example of FIG. 1, in some treatments, the same site will be irradiated by multiple optical pulses. In addition, while at any instant in time, a single pulse irradiates a single site in the example of FIG. 1, in alternate embodiments, one or more pulses can simultaneously irradiate one or more sites. No limitation on the site geometry, area or volume is intended to be implied by the layout of FIG. 1.

Figure 2:
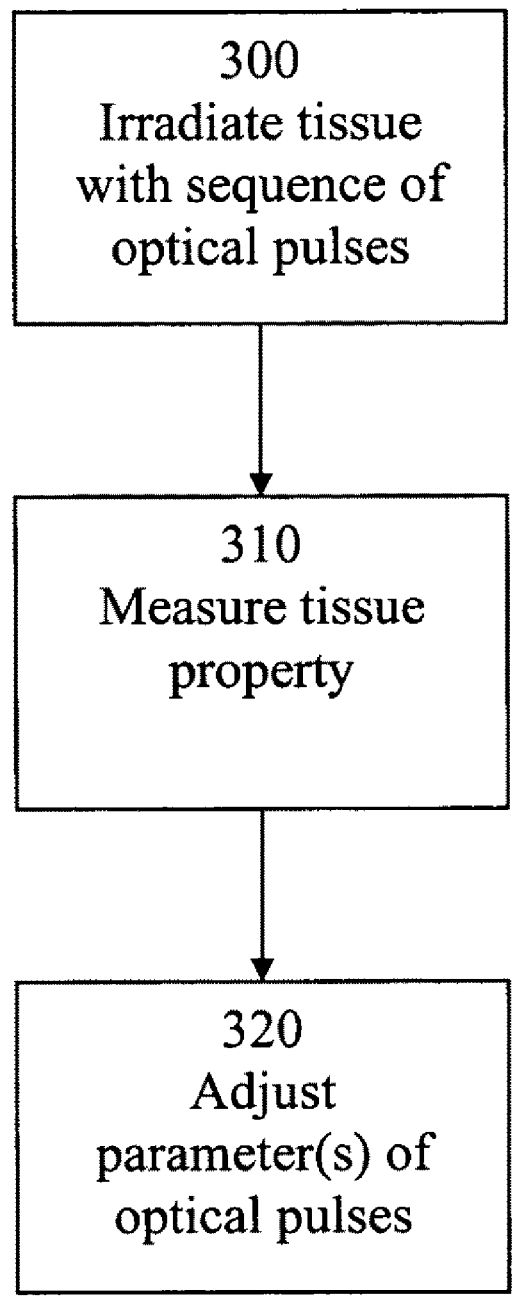
FIG. 2 is a flow diagram illustrating one method of controlling optical pulses according to the invention.

FIG. 2 is a flow diagram illustrating one method of controlling the optical pulses according to the invention. As described above, the tissue is irradiated 300 with a sequence of optical pulses that are directed to the sites 200-299. For the moment, assume that the scan of FIG. 1 is partially completed up to site 206. Sites 200-206 have already been irradiated by optical pulses and sites 207-299 are yet to be irradiated. During the irradiation sequence, measurements 310 are made of tissue properties at sites 200-206 that have already been irradiated. This data, perhaps along with other factors, is then used to adjust 320 the parameters of subsequent optical pulses in the sequence.

The already-irradiated sites contain information regarding the efficacy of the treatment, however that may be defined for the particular treatment. In one approach, measurements of one or more tissue properties may be made at any one, or all, or a partial subset of the already-irradiated sites 200-206 and measurements of one or more tissue properties may be made at any one, or all, or a partial sub-set of the sites 207-299 which have not yet been irradiated. Comparison of the before and after measurements can be used, perhaps along with other factors, to determine "on the fly" the effect the irradiation is having on the tissue. This information can also be used to control, modify or adapt the parameters for optical pulses directed to subsequent sites. Before and after measurements can be an effective way to increase the accuracy with which the assessment of the effect of the irradiation is being made. Before and after measurements can also be made by measuring the tissue property at the same site, once before irradiation and then again after irradiation, in effect measuring the change in the tissue property due to irradiation.

As described previously, different types of patterns can be used. In a preferred embodiment, the site pattern and irradiation sequence is selected so that a large area or volume of tissue is treated by applying many optical pulses to a relatively large number of relatively small sites within the treatment region in a well-defined sequence. Laser scanning or similar techniques can be used to achieve this. For further examples, see co-pending U.S. patent application Ser. No. 10/367,582, "Method and Apparatus for Treating Skin Using Patterns of Optical Energy," filed on Feb. 14, 2003, and Ser. No. 60/486,304, "Method and Apparatus for Fractional Phototherapy of Skin," filed on Jul. 11, 2003, both of which are incorporated herein by reference. The efficacy of scanning techniques in regard to the experience of both patient and practitioner is improved when the sequence of sites is covered in a relatively short time, so that the entire scan over all the sites in a sequence can be considered a single treatment.

Compared to treatments where a single large pulse or a few large pulses irradiate the entire treatment region, the use of a large number of pulses and sites typically means that there is more time available between site irradiations. For example, in some embodiments, the time lag between measurement of tissue properties and the adjustment of subsequent optical pulses can be on the order of 1 second. This relaxes the speed requirement for making adjustments to the optical pulses. While instantaneous control of pulses (i.e., adjusting the pulse parameters based on feedback from the same pulse) is generally not achievable with current technology, adaptive real-time control of subsequent pulses based on feedback from earlier pulses is well within current capability. As a result, the adverse consequences of site-to-site variations in tissue response can be significantly reduced. In cases where instantaneous control is achievable, the teachings described here can also be applied to the instantaneous control of pulses.

By testing the already-irradiated sites to set the optical pulse parameters, the accuracy with which the pulse parameters are set can be greatly improved. In the first place, the tested sites can be almost co-located with the next sites to be treated, so that the inherent site-to-site variation is reduced due to the close physical proximity. The pulse parameters will also adjust automatically during treatment to account for variations in the tissue response over longer distances within the treatment region. Also, the fact that the irradiated sites are tested during the actual treatment reduces or eliminates the need to account for the recent history of the patient or other time factors that can change between testing and treatment. Also, the need for the practitioner to select an initial set of pulse parameters can be eliminated, thereby allowing him or her to focus on other clinical features without concern for over-treating or under-treating the patient. Other advantages include greater reliability of treatment, a reduction in the rate of marginal procedures, a better patient experience, and reduced vulnerability to a low-accuracy assessment by the practitioner of the appropriate optical pulse parameters.

The pulse parameter(s) that are adjusted typically will vary depending on the application but can include the pulse energy, spot size, wavelength, temporal pulse shape, spatial pulse shape (e.g., two-dimensional intensity profile), pulse duration, focus location, depth of focus or other focusing characteristics, optical polarization, or angle of incidence on the treatment region or direction of propagation for the pulse. These parameters can also include aggregate quantities, such as the total number or density of optical pulses directed to a site or the total energy deposited at a site, or the number of pulses which simultaneously irradiate a site at any one time. Pulse parameters such as the spacing between pulses, the separation between sequentially irradiated sites, and the shape of a sequence of pulses can also be adjusted.

While FIG. 1 illustrates one example, many other variations are possible. For example, depending on the application, different tissue properties may be selected, the properties may be measured using different approaches, and different types of control can be used to adjust the parameters of the optical pulses. For example, the treatment parameters can be set as a result of a measurement of just one property of the irradiated sites, or as a result of several virtually simultaneous tests of different properties of the irradiated sites. An advantage of measuring more than one property of an irradiated site is that several treatment parameters can be optimized during treatment. For example, a measurement of skin surface temperature in conjunction with a measurement of tissue denaturation at depth would allow the laser pulse length and energy to be adjusted to achieve the most beneficial effect at depth while avoiding skin surface damage due to excessive surface temperature. Using multiple measurements in this way is amenable to the use of artificial intelligence in the control algorithms to enable the treatment system to "learn" the optimum parameters for treatment while the treatment is progressing, or to learn decision rules for determining the optimum parameters.

A preferred approach is to make measurements of the tissue property before and after optical irradiation, but during a single treatment or scan. On comparing the measurements so made, and possibly taking account of other factors, the change in the tissue as a result of optical irradiation is assessed, and the optical irradiation parameters for the next site or set of sites are adjusted for best results. In one approach, measurements are made at the last site to be irradiated and that data is used to adjust the irradiation parameters for the next site. In an alternate approach, measurements are made over a number of previously irradiated sites either simultaneously or individually and adjustments are made that would apply to a number of subsequent sites.

In particular, a preferred embodiment makes measurements of the tissue changes over a set of N previously irradiated sites, and updates the optical irradiation parameters slowly by forming a weighted average over the results of the measurements over the aforementioned N sites and using this weighted average to update the irradiation parameters. In this way, the updating process can be stabilized and better matched to any expected site-to-site variations in tissue response.

A preferred weighting is exponential. Consider first the use of a single control parameter, obtained from a measurement of one property of the irradiated site. If X is the value of the control parameter used to set the irradiation parameters just before site J is irradiated (site 207 in FIG. 1), and $x_j$ is the measured value of this parameter at the site j, then:

$$X = \Sigma(x_j w_j)/\Sigma w_j, \quad \text{(Eqn. 1)}$$

where the sum is over a certain number of already-irradiated sites ($1 \leq j < J$), ordered in the sum in the order of their irradiation, and the weighting function is $$w_j = \exp(-\alpha(J-j)) \quad \text{(Eqn. 2)}$$

Here, $\alpha$ is a parameter that limits the information to roughly the previous $1/\alpha$ sites in the sequence although the weighted average can also consider more or less than the $1/\alpha$ sites. By selecting $\alpha$, the updating process can take into account variations in the tissue response over the area or volume to be treated, as well as improving the accuracy of the control parameter X by improving the statistics of its measurement. Other treatments of the set $\{x_j\}$ to obtain X can also be used. However, for linearly followed sequences, the exponential weighting or an equivalent method of obtaining X from $\{x_j\}$ is generally preferred.

In one approach, the calculated value of X is compared with one or more pre-determined values $X_0$. Based in part on that comparison, and possibly also the number of previously irradiated sites, a parameter of the irradiation pulses for the next site is adjusted.

One reason for deviating from a true exponential weighting might be a time delay in obtaining the measured value $x_j$ associated with the speed the measurement can be made. For example, if the scan irradiates the treatment region at the rate of 250 sites per second, and the measurement process takes 10 milliseconds for each site, the data from the previous four sites will not be available in time to be used at the next site. In this case, a preferred method is to exclude those sites from the weighted average for the control parameter X.

In some treatments, the sequence of sites may not be followed linearly over the region to be treated. For example, if the sites cover an area relatively uniformly, but it is desirable for the next site not to be adjacent to the last site irradiated, or to be somewhat distant, other weighting functions can be more appropriate. For example, in FIG. 1, site 203 is irradiated next after site 202 but, due to the physical proximity, measurements from site 200 may be a better predictor and therefore should be more heavily weighted. One alternative is to use an exponential weighting based on distance rather than time or sequence number:

$$w_j = \exp(-\alpha D(J,j)) \quad \text{(Eqn. 3)}$$

where $D(J,j)$ is the linear distance between the sites J and j, raised to a power preferably between 1 and 3. This weighting ensures that control information is obtained only from already-irradiated sites that are adjacent to the next site to be irradiated. Preferably, only data that is both available and relevant are included in the weighted average for X.

The information represented by the control parameter X can be used for end-point detection. As an example of end point detection, assume that if X is less than some value $X_1$ the tissue is considered to be under-treated, if greater than some other value $X_2$, over-treated. A favorable treatment would be expected if X lies in the range $X_1<X<X_2$. If X lies outside of this range, some parameter Y of the irradiation is adjusted until X again lies in the target range. For treatments that use the heating effect of a laser pulse, Y may be the laser pulse energy or pulse length. The process of determining X and testing to see if it lies in the favorable range is one example of end-point detection.

The technique of adjusting the irradiation parameters so that as the scan proceeds X is maintained within the favorable range can be implemented using different types of well-known control algorithms. For example, control might be implemented by monitoring the relevant irradiation parameter Y and the parameter X, on a shot-by-shot basis, and creating a calibration table. Then, a value of X lying in the favorable range can be achieved by setting Y in the range obtained from the calibration table.

Another way to adapt the irradiation pulse takes account of the innately statistical nature of the treatment. Consider a treatment of wrinkles in the skin where a laser is used to heat the tissue, causing certain beneficial changes in the collagen. In this case, a control parameter X might be a measurement of the birefringence of the skin, or its electrical capacitance or its ultrasound reflectivity or a combination of these parameters. Assume that the irradiation parameter controlling the heating effect of the laser is the laser pulse energy, because the temperature rise in the tissue is roughly proportional to the laser pulse energy (E). The control process may involve setting the pulse energy according to a simple formula where it is increased steadily if X is too low, and decreased steadily if X is too high. That is $X<X_0$:$E$ increased by $K(X_0-X)$ $X>X_0$:$E$ decreased by $K(X-X_0)$   (Eqn. 4)

where $X_0$ is the midpoint of the favorable range of X, i.e., $X_0=(X_1+X_2)/2$, and K is a parameter set by field experience so that the normal fluctuations expected for X remain within the favorable range in a statistical sense. This procedure preferably uses a weighted average for X as described above, to reduce the incidence of incorrectly-irradiated sites associated with fluctuations in the tissue response. The laser pulse energy may be controlled either by adjusting the laser power, or the optical pulse length, at the discretion of the laser engineer, to optimize the irradiation tool that is used to implement the treatment.

Many types of control algorithms can be used, based on different types of measured properties and controlled parameters. In general, assume that a set $\{X^{(k)}, k=1,N\}$ of N measured tissue properties is used to control a set $\{Y^{(k)}, k=1,M\}$ of M irradiation parameters. Usually, $M<=N$. Control algorithms for the multiple variable case (N>1 or M>1 or both) are more complex than for the case where N=M=1, but many such algorithms exist and are well-known. Concepts such as the exponential weighting described above can be straightforwardly generalized to the multiple variable case.

The use of measurements $\{X\}$ to control parameters $\{Y\}$ is also amenable to the use of sophisticated control logic, and also to utilizing the techniques of artificial intelligence (AI). Some such algorithms can "learn" the optimum treatment parameters for a particular patient during the treatment itself. As the scan proceeds, the treatment parameters will vary, for example as a result of random effects or as a result of deliberate "dithering" by the control system. The control system has access to both statistical information and to information on the correlations of the measured tissue response with the treatment parameters. Such information allows the system to optimize the treatment parameters by the use of moving simplex algorithms to optimize the treatment.

Also, if there are undesirable results of irradiation that must be avoided, simplex algorithms can also be used to implement constraints, so that the undesirable irradiation conditions are avoided. One example is the avoidance of surface damage to the skin while maintaining beneficial results below the tissue surface, for which simplex algorithms are a natural choice.

Other types of algorithms are possible, such as neural nets and fuzzy logic. The capability offered by AI control procedures enables the system to adjust the treatment finely to individual tissue characteristics. They also enable the system to adjust the treatment finely to those tissue characteristics that the patient presents on the day and at the time of treatment, or to adjust the treatment protocols to account for differences in tissue characteristics at different locations in the treatment scan, as the treatment scan proceeds. AI algorithms can enable the system to "learn" the optimum treatment parameters for each patient.

In one implementation, this data is stored in a clinically approved format and made available for subsequent retrieval. Thus, an appropriately de-personalized history of treatment protocols for each patient would be available in a database for further study. Alternately, it could be retrieved for use in subsequent treatments of the patient, for example as a starting point for adjusting parameters. One advantage of AI algorithms is that many AI algorithms can determine the relationship between the desired tissue response, such as denaturation, and the parameters or properties being measured as control parameters, at least in part, during the scan.

The measurements of tissue response necessary for effective control of the irradiation process may be effectively implemented by including appropriate modules (hardware, software, or other) in the tool that delivers the optical pulses to the tissue. These modules are preferably located close to the tissue surface and adjacent to the optics through which optical pulse is delivered to the tissue. Then, as the point of application of the optical pulses ranges over the scan, the necessary sources and detectors also scan the tissue in the same manner and are conveniently located to perform their function.

Figure 3A:
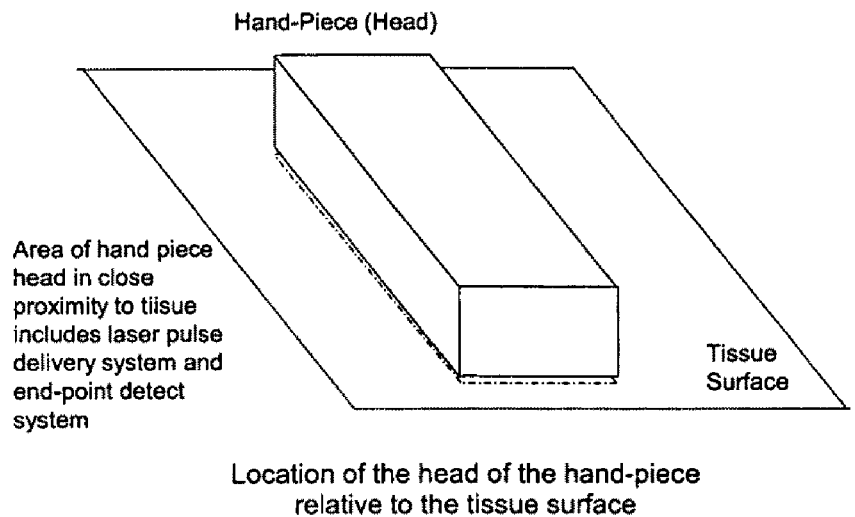
FIGS. 3A-3C are diagrams illustrating a layout of handpieces according to the invention.
Figure 3B:
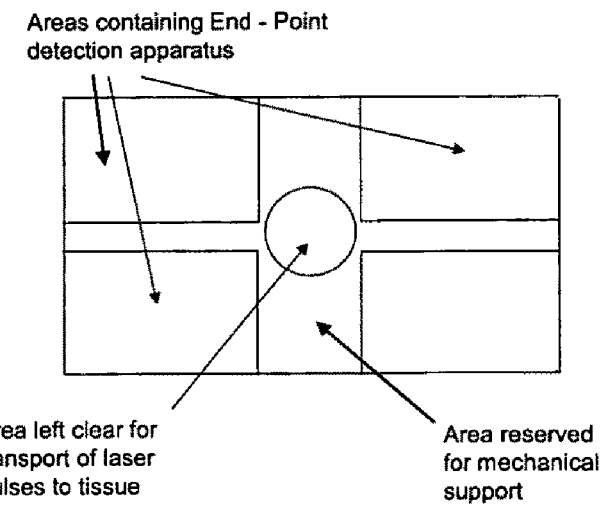
Figure 3C:
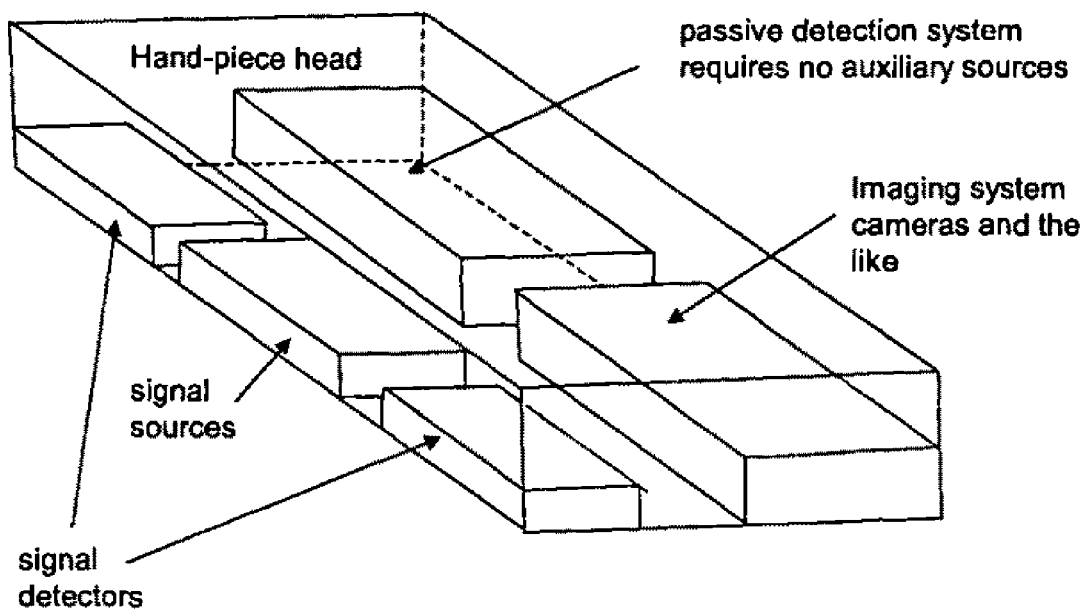
Figure 4:
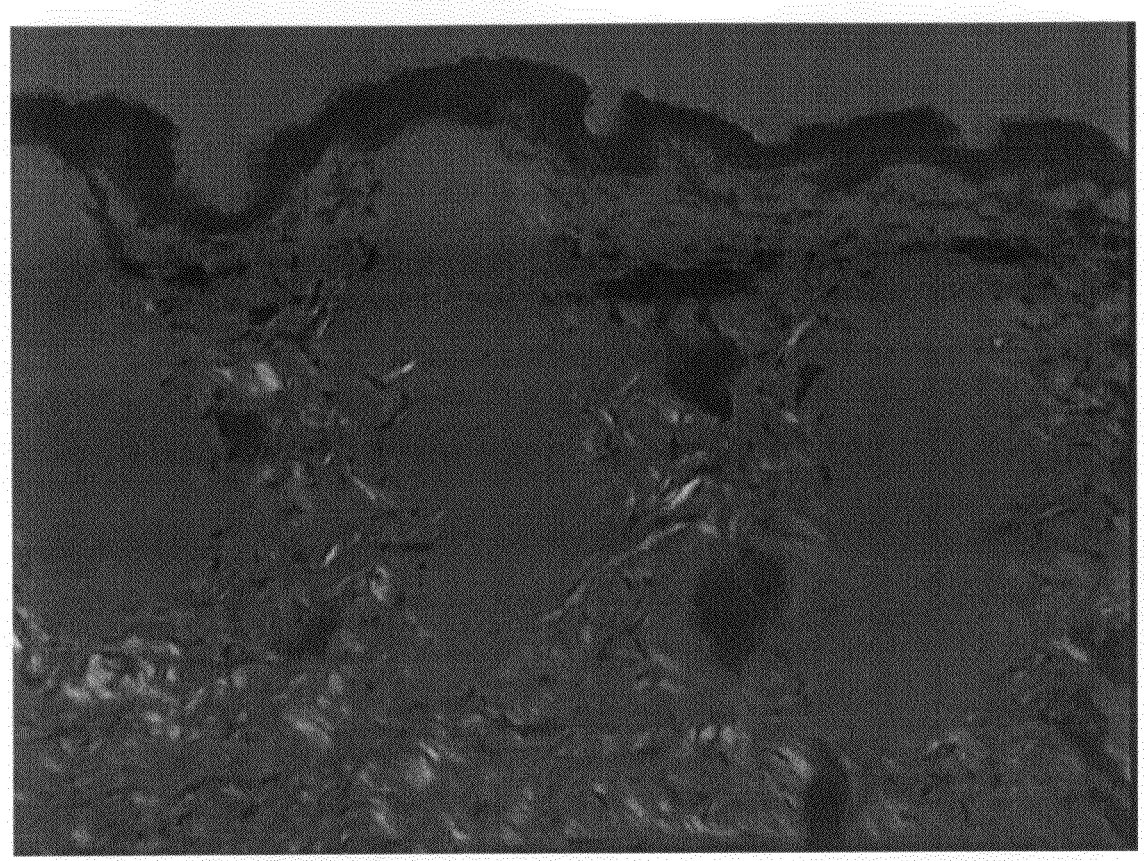
FIG. 4 illustrates change in birefringence due to coagulation.
Figure 5:
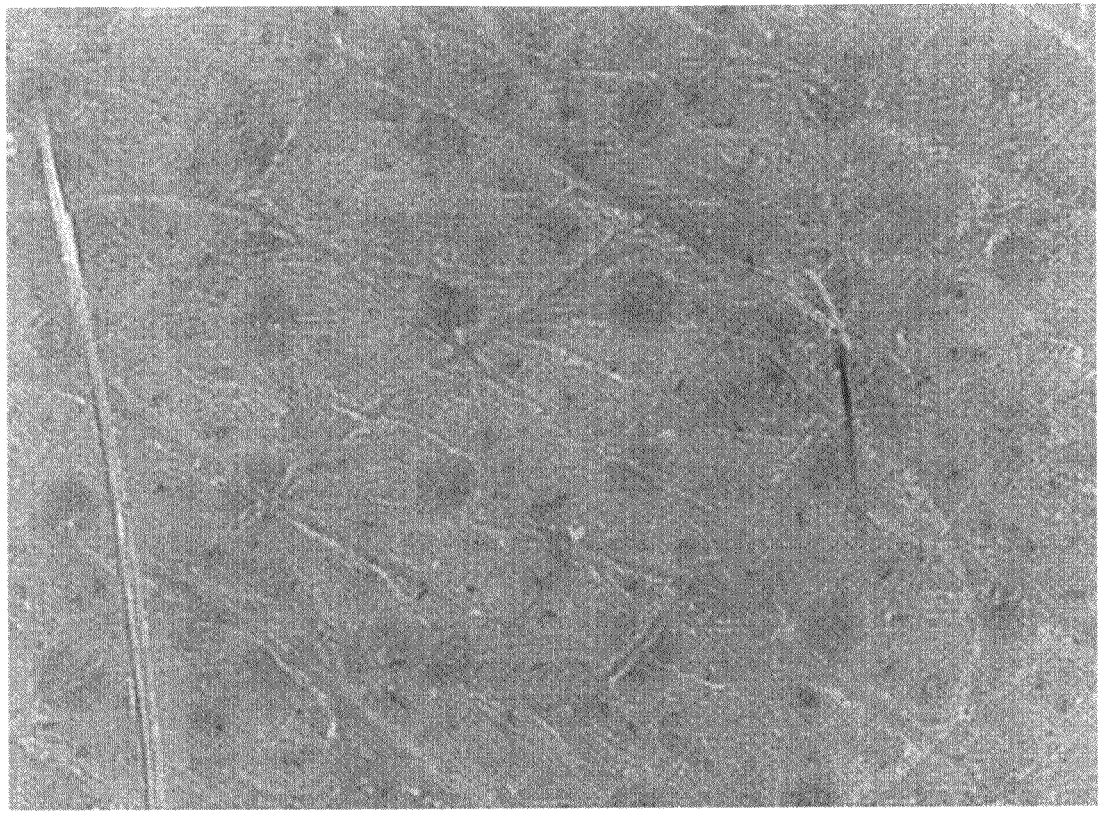
FIGS. 5-6 illustrate microscopy of the skin surface
Figure 6:
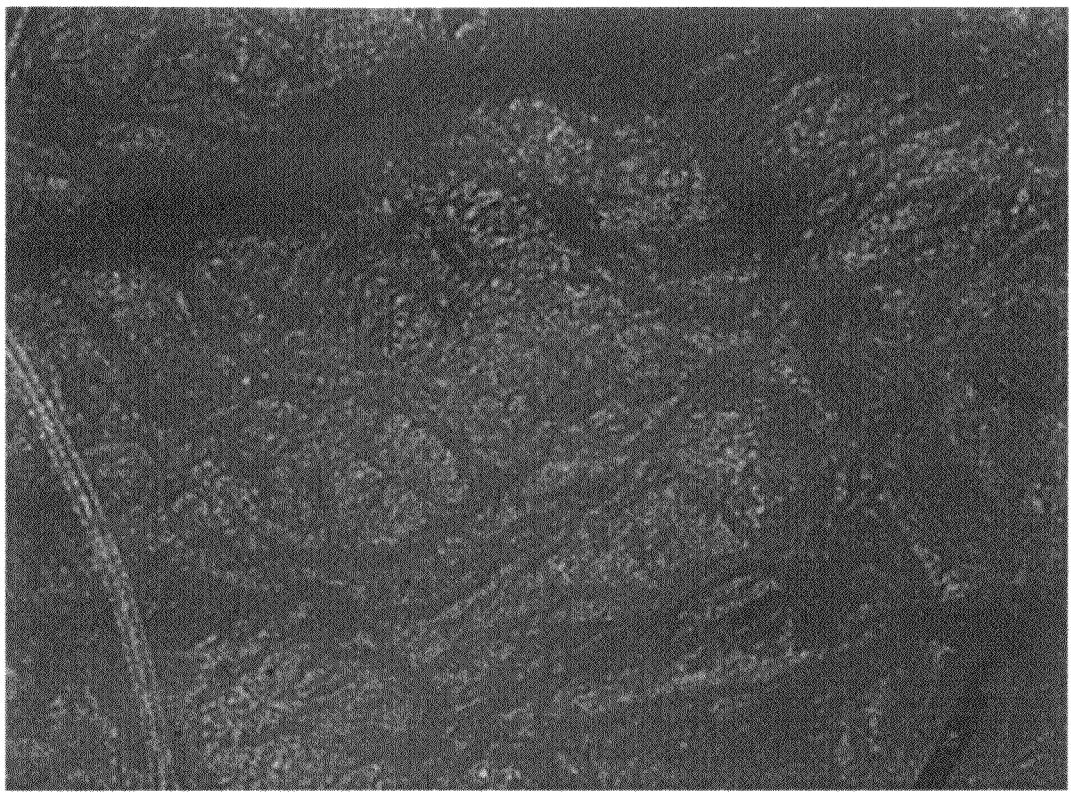
Figure 7:
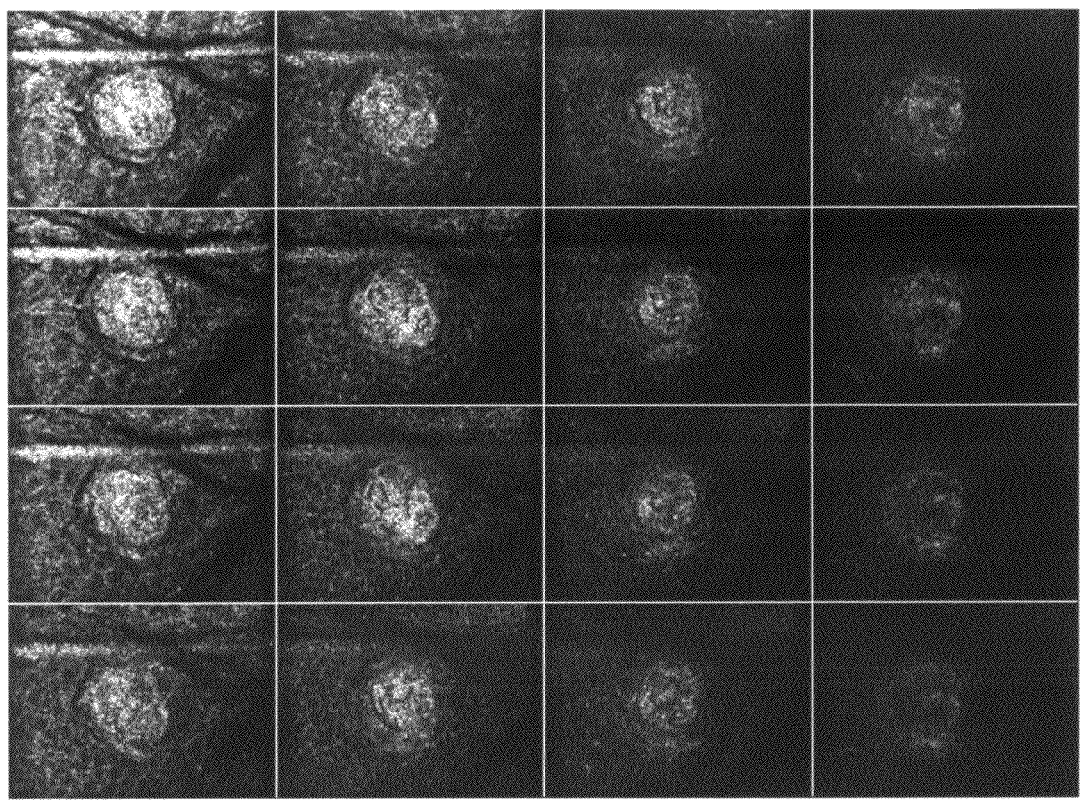
FIG. 7 illustrates confocal microscopy to varying depth in the skin.
Figure 8:
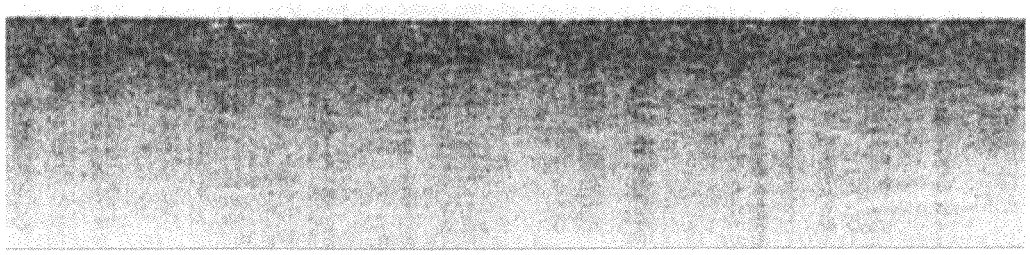
FIG. 8 illustrates optical coherence tomography.
Figure 9:
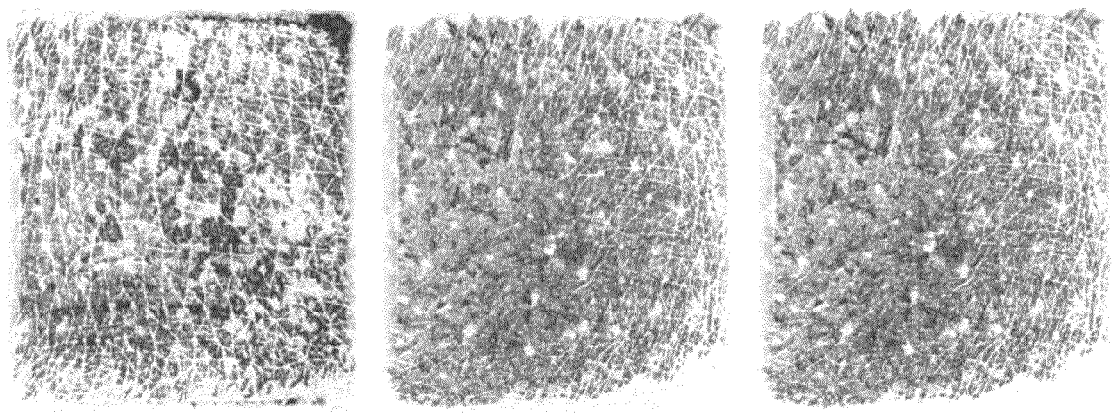
FIGS. 9-10 illustrate electrical capacitance measurements of human skin.
Figure 10:
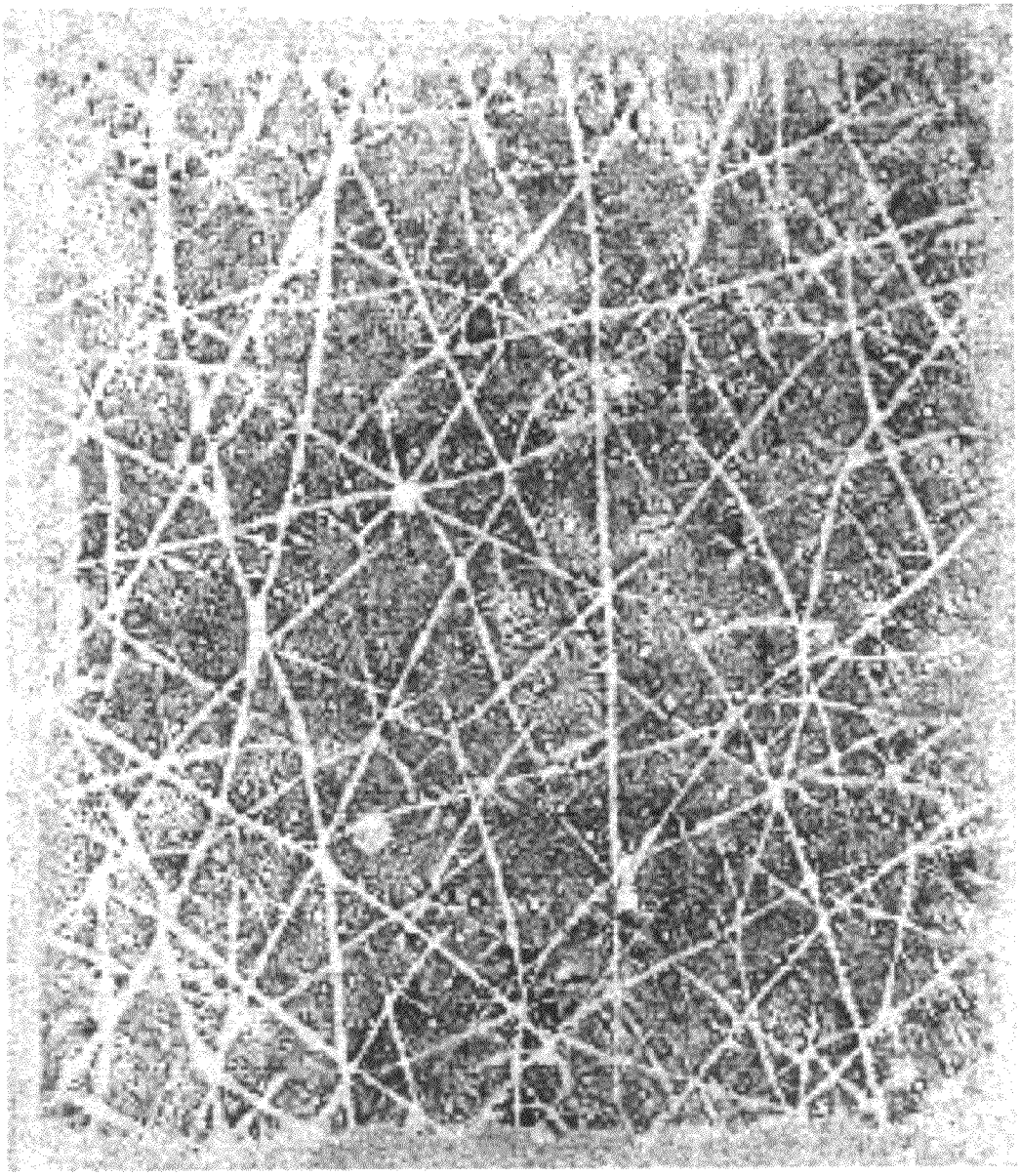

This is illustrated in FIGS. 3A-3C. For example, FIG. 3A illustrates the location of the head of a hand-piece that is moved over the tissue during the performance of a treatment scan. The head contains the optics for delivery of the laser pulses and may contain various other elements for ascertaining and controlling the precise location of the sites where the laser pulses are applied. The head preferably lies close to the tissue and is preferably either in contact with the tissue or maintained a fixed distance from the tissue surface. Proximity to the tissue enhances the positional accuracy of the sites and optimizes control of the boundaries of the volume treated at each site. Proximity also enhances the accuracy and reliability of end-point detection, in general.

FIG. 3B illustrates the active area of the head, the surface of the head right next to the tissue. The pulse delivery optics occupies only a portion of this area, leaving a considerable area for other functionalities. In this example, one such functionality is a precise positioning capability for the irradiation sites. Another such functionality includes passive detection methods that do not require any signal sources other than those already present, which include the room light, thermal radiation from the tissue, and the light from the optical pulses.

Yet another such functionality includes active detection methods, where the signals detected originate from auxiliary sources. Such auxiliary sources are preferably but not necessarily located within the hand-piece head.

A perspective view of another hand-piece head is shown in FIG. 3C. Technologies that may be incorporated in this manner include ultrasound, optical detection methods, and thermal detection methods. While a specific geometry is illustrated in FIGS. 3A-3C, other configurations of hardware that permit the end-point detection to be adjacent to the optical pulse delivery hardware are possible. These include circular or oval apertures and three-dimensional overlays of hardware boards. In an alternative arrangement, the source and detectors may be remote from the hand-piece head, but connected to it via optical fibers. Then, the hand-piece head contains the terminated optical fibers for the source and the detectors, located adjacent to the treatment delivery optics.

Other modules may also be located remotely from the hand-piece or beam delivery tool. For example, the optical source that generates the optical pulses may be remotely located, with the pulses delivered by optical fiber. The controller that implements the control algorithm may also be remotely located. In an alternate embodiment, if the controller is simple enough, it can be implemented in hardware and/or software resident in the hand-piece or beam delivery tool.

Turning now to different tissue properties, many means of testing the tissue can be utilized. Such techniques can include optical coherence tomography (OCT), confocal microscopy, optical microscopy, optical fingerprinting, and ultrasound. Tissue properties that may be measured include for example temperature, mechanical density, color, birefringence, opacity, reflectivity, absorption, extinction, scattering, albedo, polarizability, dielectric constant, capacitance, chemical balance, elastic properties, fractions of different materials (e.g., water, melanin, hemoglobin, oxyhemoglobin and foreign matter) and the properties of fluids introduced into the tissue.

In one embodiment, the reflection of high frequency acoustic waves (ultrasound) by the tissue is used to determine in part the local sound speed in the tissue. The local sound speed depends on the chemical state of the tissue, its density, and the sharpness of boundaries in the tissue between regions of different sound speed. All or some of these attributes of the tissue can be affected by optical irradiation. For example, if the dermis is irradiated, causing changes in the collagen fibers in the skin, these three attributes of the tissue are also changed (as well as other attributes) and this change can be detected by comparing the reflection of ultrasound before and after irradiation. In particular, the change in the strength of the reflection increases steadily with the fraction of the skin that has been affected by the irradiation. In this way, the fraction of affected tissue may be continuously monitored and used (perhaps along with other factors) to control the irradiation of subsequent sites in the sequence, thereby permitting adjustment of the irradiation parameters from the beginning to the end of the scan. It is preferable for the ultrasound heads and delivery optics to be adjacent in the same head.

In another embodiment, the optical reflection of the tissue at specified wavelengths is measured. For example, if the dermis is irradiated with the intent of treating blood vessels, the optical reflection of the tissue in the near-infrared part of the electromagnetic spectrum will change as the blood chemistry is altered by the irradiation. By measuring the infrared reflection spectrum at wavelengths relevant to detecting changes in blood chemistry, a measure is obtained of the amount of blood whose chemistry has been altered, and the extent to which it has been altered. The sources may produce either a single color (wavelength) or a range of wavelengths (spectrum), and each detector is preferably fitted with a wavelength filter to improve the signal-to-noise ratio of the detection. In one implementation, the light reflected from the tissue is compared with the strength of the source detectors, and the wavelengths detected are substantially the same as those of the source. Changes in the reflectivity may occur as a result of the change in the scattering of light in the tissue associated with protein denaturation. Protein denaturation is an important feature of several laser dermatological procedures, especially those involving collagen. It is preferable, in this invention, for the optical reflectivity sources and detectors to be adjacent to the laser pulse delivery optics in the same head. Temporal gating or optical blocking filters can be used to prevent the optical pulses from overwhelming the reflectivity measurement.

Another property of tissue associated with denaturation of collagen is optical birefringence. Birefringence is present in normal collagen tissue, but disappears when tissue is coagulated. To use birefringence for end-point detection, the light source is typically linearly optically polarized, and optical polarizers are used to select the orthogonal polarization for detection. The treatment pulses may possibly be used as the source of light for birefringence measurements, but a more accurate procedure utilizes a highly directional source at a wavelength that has weak absorption and scattering, and so penetrates deeply into the tissue, such as the 1064 nm wavelength of a Nd:YAG laser. The detector is also preferably highly directional in operation. Collagen denaturation results in a reduction of return signal, which may be used to measure the tissue response.

In another preferred embodiment, the optical fluorescence spectrum of the tissue is measured. The light from the sources is typically monochromatic, and of a short time duration. The light emitted from the tissue in response to the source pulse is typically measured at a different wavelength, and possibly as a function of the delay time after the source has ceased. The optical fluorescence spectrum is a determinant of the chemical species, and so can detect changes in the chemical composition within the tissue caused by the illumination treatment. The measurement of a fluorescence spectrum is familiar to one of ordinary skill in the art of laser/electro-optic technology. The arrangement of sources and detectors is very similar to that for reflectance or birefringence measurements.

Microscopy of the tissue surface can also be used. Measurements can be made of the image on the surface, or of the temperature of the surface using a thermal camera. The effect at the surface of skin after a treatment scan can be characterized by its contrast to determine the level of tissue response. This type of measurement is passive, but is more reliable if an auxiliary light source is used to enhance the signal-to-noise of the image contrast. Microscopy may be used to select a small region of the image for size, local color, or local reflectivity (as distinct from a regional average reflectivity measurement described above). For treatments that cause lesions below the surface, the same technique may also apply, as there is often an effect on the tissue at the surface even though the most intense changes in the tissue lie below the surface. For a deeper lesion, up to 1 mm below the surface, the technique of confocal microscopy may be used to characterize its shape.

Yet another means for characterizing tissue response is optical coherence tomography (OCT), for example as integrated into the hand-piece head through the use of dispersionless fiber optics. For larger lesions, OCT offers the opportunity to make measurements at depths into the skin where other technologies fail as a result of optical scattering.

Yet another means for characterizing the state of tissue is by capacitive sensing, which uses technology developed for fingerprint detection. Capacitive sensing utilizes the electrical capacitance of the tissue as the measured tissue parameter, to be used in a similar manner as the optical reflectivity or the ultrasound reflectivity, as described previously. The appearance of surface images created using a capacitive sensor represents a means of characterizing a sub-surface, or dermal lesion created by an optical pulse, in the manner described herein. Furthermore, by using lower spatial frequency electrode patterns, blood vessels and other subsurface structures can be observed if the dielectric constant of the structure differs from the immediate surroundings. This makes superficial blood vessels visible as well.

Many other tissue properties can also serve as a means to determine the effect of the optical irradiation on the tissue. Foreign matter can also be introduced into the tissue, by injection or other means, in order to provide a means of determining and utilizing the tissue response. Examples of foreign matter include chemicals taken orally that infuse the tissue and provide an optical fluorescence specific to a property of the tissue of interest, such as sugar concentration, hemoglobin concentration, or white or red cell count. Other examples include fluids applied externally to the tissue and absorbed into the tissue.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims.

What is claimed is:

1. A method for automatically controlling treatment of tissue with optical pulses, comprising:
   irradiating a first site in a portion of tissue with a first optical pulse;
   following the irradiation, automatically making a measurement of a tissue property at the first site;
   based on the measurement, automatically adjusting a parameter of a second optical pulse according to an algorithm selected from the group consisting of a moving simplex algorithm, a neural net algorithm, and a fuzzy logic algorithm;
   irradiating a second site in the portion of tissue with the second optical pulse in order to provide treatment of the tissue at a pre-determined treatment level;
   irradiating other sites in the portion of tissue with other optical pulses;
   following the irradiation, automatically making measurements of the tissue property at the other sites; and
   taking a weighted average of the measurements,
   wherein the step of automatically adjusting the parameter of the second optical pulse is based on the weighted average of the measurements.

2. The method of claim 1, wherein irradiating the first site with the first optical pulse and irradiating the second site with the second optical pulse both occur by laser scanning.

3. The method of claim 1, further comprising:
   irradiating the first site with a first sequence of multiple optical pulses that includes the first optical pulse.

4. The method of claim 1, further comprising:
   irradiating multiple sites with a first sequence of optical pulses, said irradiation including irradiating the first site with the first optical pulse.

5. The method of claim 1, wherein the parameter of the second optical pulse includes a parameter selected from the group consisting of an energy of the optical pulse, a duration of the optical pulse, a temporal shape of the optical pulse, a spatial shape of the optical pulse, a propagation direction of the optical pulse relative to the tissue surface, a focusing characteristic of the optical pulse, a polarization of the optical pulse, and a wavelength spectrum of the optical pulse.

6. The method of claim 1, wherein the tissue property includes a property selected from the group consisting of mechanical density, electrical capacitance, dielectric constant, birefringence, opacity, optical reflectivity, absorption, extinction, elasticity, water fraction, melanin fraction, hemoglobin fraction, oxyhemoglobin fraction, and fraction of foreign matter.

7. The method of claim 1, wherein the tissue property includes a temperature of the tissue.

8. The method of claim 1, wherein automatically making the measurement of the tissue property at the first site comprises:
   making a measurement of a change in the tissue property at the first site.

9. The method of claim 8, wherein automatically making the measurement of the change in the tissue property at the first site comprises:
   making a measurement of a change in the tissue property before irradiation of the site by the first optical pulse and after irradiation of the site by the first optical pulse.

10. The method of claim 1, wherein making the measurement of the tissue property comprises:
    measuring two or more tissue properties.

11. The method of claim 10, wherein automatically adjusting the parameter of the second optical pulse comprises:
    automatically adjusting two or more parameters of the second optical pulse based on the measurements.

12. The method of claim 1, further comprising:
    determining a characteristic of the tissue based on the measurement.

13. The method of claim 12, wherein automatically adjusting the parameter of the second optical pulse comprises:
    automatically adjusting a parameter of the second optical pulse in response to the determined characteristic.

14. The method of claim 1, wherein the measurement and the irradiation by the second optical pulse are separated by less than 1 second.

15. The method of claim 1, wherein the weighted average is an exponential weighted average.

16. The method of claim 1, wherein the weighted average is weighted according to time.

17. The method of claim 1, wherein the weighted average is weighted according to distance from the second site.

18. A method for automatically controlling treatment of tissue with optical pulses, comprising:
    irradiating a first site in a portion of tissue with a first optical pulse;
    following the irradiation, automatically making a measurement of a tissue property at the first site;
    based on the measurement, automatically adjusting a parameter of a second optical pulse;
    irradiating a second site in the portion of tissue with the second optical pulse in order to provide treatment of the tissue at a pre-determined treatment level;

irradiating other sites in the portion of tissue with other optical pulses;

following the irradiation, automatically making measurements of the tissue property at the other sites; and taking a weighted average of the measurements, wherein the step of automatically adjusting a parameter of the second optical pulse is based on the weighted average of the measurements.

19. The method of claim 18, wherein the weighted average is an exponential weighted average.

20. The method of claim 18, wherein the weighted average is weighted according to time.

21. The method of claim 18, wherein the weighted average is weighted according to distance from the second site.

22. The method of claim 18, wherein irradiating the first site with the first optical pulse and irradiating the second site with the second optical pulse both occur by laser scanning.

23. The method of claim 18, further comprising:

irradiating the first site with a first sequence of multiple optical pulses that includes the first optical pulse.

24. The method of claim 18, further comprising:

irradiating multiple sites with a first sequence of optical pulses, said irradiation including irradiating the first site with the first optical pulse.

25. The method of claim 18, wherein the parameter of the second optical pulse includes a parameter selected from the group consisting of an energy of the optical pulse, a duration of the optical pulse, a temporal shape of the optical pulse, a spatial shape of the optical pulse, a propagation direction of the optical pulse relative to the tissue surface, a focusing characteristic of the optical pulse, a polarization of the optical pulse, and a wavelength spectrum of the optical pulse.

26. The method of claim 18, wherein the tissue property includes a property selected from the group consisting of mechanical density, electrical capacitance, dielectric constant, birefringence, opacity, optical reflectivity, absorption, extinction, elasticity, water fraction, melanin fraction, hemoglobin fraction, oxyhemoglobin fraction, and fraction of foreign matter.

27. The method of claim 18, wherein the tissue property includes a temperature of the tissue.

28. The method of claim 18, wherein automatically making the measurement of the tissue property at the first site comprises:

making a measurement of a change in the tissue property at the first site.

29. The method of claim 28, wherein automatically making the measurement of the change in the tissue property at the first site comprises:

making a measurement of a change in the tissue property before irradiation of the site by the first optical pulse and after irradiation of the site by the first optical pulse.

30. The method of claim 18, wherein making the measurement of the tissue property comprises:

measuring two or more tissue properties.

31. The method of claim 30, wherein automatically adjusting the parameter of the second optical pulse comprises:

automatically adjusting two or more parameters of the second optical pulse based on the measurements.

32. The method of claim 18, further comprising:

determining a characteristic of the tissue based on the measurement.

33. The method of claim 32, wherein automatically adjusting the parameter of the second optical pulse comprises:

automatically adjusting a parameter of the second optical pulse in response to the determined characteristic.

34. The method of claim 18, wherein the measurement and the irradiation by the second optical pulse are separated by less than 1 second.

* * * * *